United States Patent [19]
Engelhardt et al.

[11] Patent Number: 6,166,278
[45] Date of Patent: *Dec. 26, 2000

[54] USE OF NATURALLY ACID SMECTITES TO REMOVE OLEFINS FROM AROMATICS OR AROMATIC MIXTURES AND PROCESSES THEREWITH

[75] Inventors: Thomas Engelhardt, Freising; Uwe Flessner, München; Reinhard Hähn, Vilsheim; Werner Zschau, Steinebach, all of Germany

[73] Assignee: Süd-Chemie A.G., Germany

[*] Notice: This patent is subject to a terminal disclaimer.

[21] Appl. No.: 08/930,965

[22] PCT Filed: Feb. 28, 1996

[86] PCT No.: PCT/EP96/00808

§ 371 Date: Sep. 30, 1997

§ 102(e) Date: Sep. 30, 1997

[87] PCT Pub. No.: WO96/30321

PCT Pub. Date: Oct. 3, 1996

[30] Foreign Application Priority Data

Mar. 31, 1995 [DE] Germany ............... 195 12 137

[51] Int. Cl.⁷ .................................................. C07C 7/163
[52] U.S. Cl. .................. 585/259; 585/820; 585/823; 585/829; 585/520; 585/532; 585/533; 502/79; 502/80; 502/81; 502/85; 502/60
[58] Field of Search ..................... 585/820, 823, 585/829, 520, 532, 533, 259; 502/79, 80, 81, 85, 60

[56] References Cited

U.S. PATENT DOCUMENTS

| | | | |
|---|---|---|---|
| 3,835,037 | 9/1974 | Fairweather et al. | 208/260 |
| 4,193,454 | 3/1980 | Goldstein | 166/302 |
| 4,531,014 | 7/1985 | Gregory et al. | 585/415 |
| 4,795,550 | 1/1989 | Sachtler et al. | 208/307 |
| 5,180,864 | 1/1993 | Sanderson et al. | 585/10 |
| 5,749,955 | 5/1998 | Shaked et al. | 106/287 |

FOREIGN PATENT DOCUMENTS

| | | |
|---|---|---|
| 0 116 469 | 8/1984 | European Pat. Off. . |
| 0 449 453 | 10/1991 | European Pat. Off. . |
| 23 85789 | 10/1978 | France . |
| 25 99275 | 12/1987 | France . |
| 10 94389 | 12/1960 | Germany . |
| 3728812 | 5/1989 | Germany . |
| 285241 | 12/1990 | Germany . |
| 299382 | 5/1992 | Germany . |
| 63-310837 | 12/1987 | Japan . |
| 1162945 | 9/1969 | United Kingdom . |

Primary Examiner—Hien Tran
Assistant Examiner—Nadine Preisch
Attorney, Agent, or Firm—Scott R. Cox

[57] ABSTRACT

A catalyst for removing olefins from aromatic compounds or mixtures of aromatic compounds wherein the catalyst is a naturally acidic smectite clay containing exchangeable cations wherein the naturally acidic smectite clay has a cation exchange capacity of 40 to 80 meq./100 g. and wherein the exchangeable cations include 5 to 70 meq./100 g. of $Al^{3+}$ cations, a process for the preparation of this catalyst including treating a naturally acidic smectite clay with an aluminum salt solution wherein the salt solution includes $Al^{3+}$ ions at a concentration of at least 10 meq./100 g. of the catalyst, and a process for the removal of olefins from aromatic compounds or mixtures of aromatic compounds using the above-described catalyst.

22 Claims, 1 Drawing Sheet

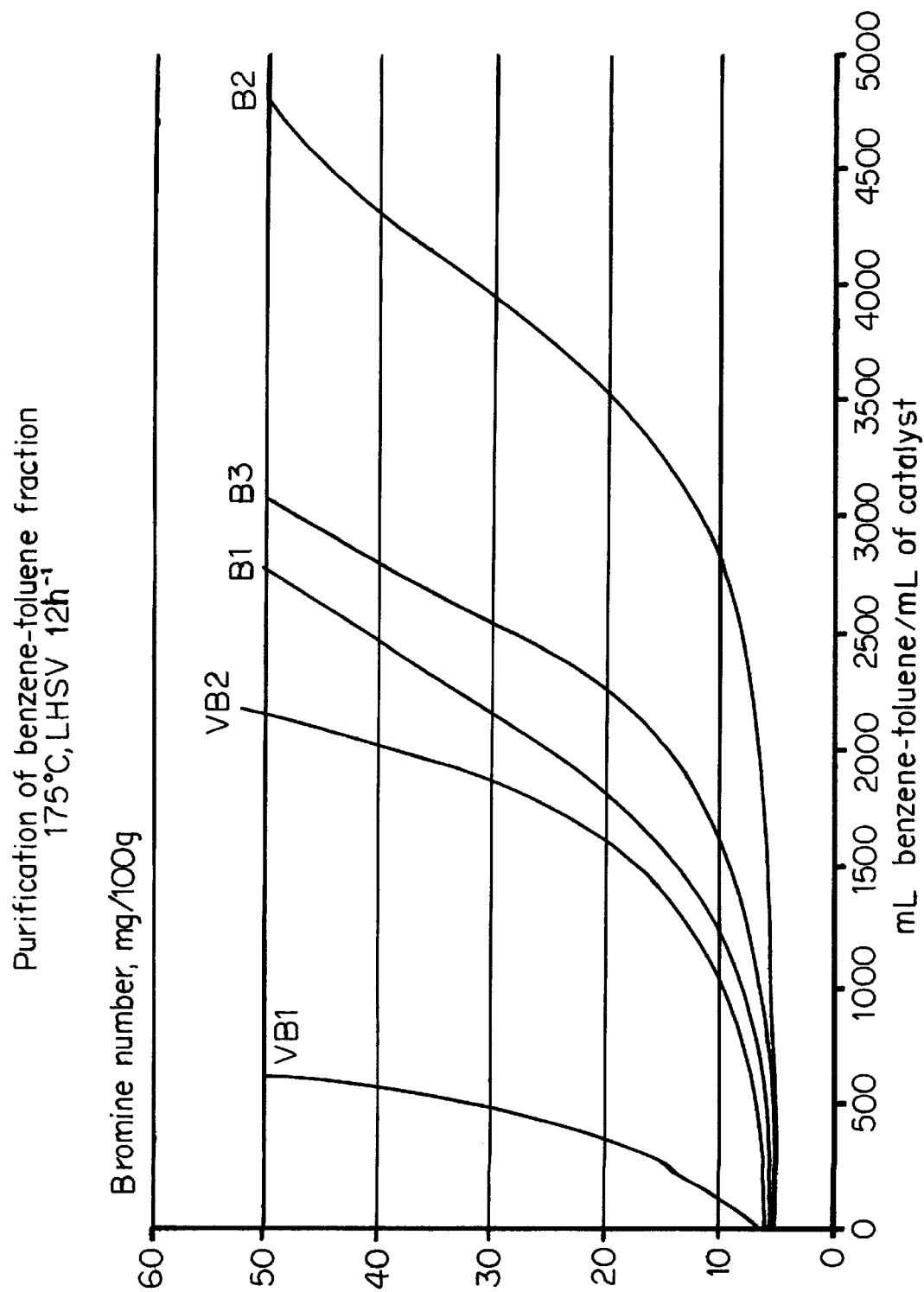

USE OF NATURALLY ACID SMECTITES TO REMOVE OLEFINS FROM AROMATICS OR AROMATIC MIXTURES AND PROCESSES THEREWITH

The invention concerns the use of naturally acid smectites to eliminate olefins from aromatics or aromatic mixtures.

The most significant industrial aromatics benzene, toluene and xylenes (BTX) are now almost exclusively produced by catalytic or thermal conversion of appropriate petroleum fractions.

In so-called catalytic reforming a paraffinic naphtha fraction is treated at about 400° C. with noble metal-coated catalysts. Aromatics are formed from the saturated hydrocarbons during this catalytic process. These aromatics are then separated from the nonaromatics by extraction or crystallization and further processed by distillation.

The sulfolane process has emerged as the most important process for extractive separation of benzene-toluene mixtures (Ullmann's Encyklopadie der Technischen Chemie, Vol. 8 (1974), p. 395).

Limited amounts of olefins are also formed during catalytic reforming in addition to the desired aromatics. These olefins, whose content generally lies below 1%, interfere with subsequent processing and must be removed. Since the undesired olefins have roughly the same boiling points as the aromatics, distillative separation is not possible.

Catalytic treatment with alkaline earth metal aluminosilicates, for example, activated smectites in granulate form, has emerged as an economical process worldwide for elimination of these olefins. The aromatic stream is passed through a fixed bed reactor at about 150–200° C. The granulates act as catalyst; the undesired olefins are converted to higher boiling products that can then be easily separated by distillation.

It is known that natural or synthetic alkaline earth metal aluminosilicates are preferably used as suitable catalysts for elimination of olefins. A wide variety of methods have been described using acid-activated bentonites (bleaching earth). For example GB-1 162 945 and DE-C-22 36 996 can be referred to in this connection. The commercial products for aromatic purification are generally granulated acid-activated bentonites, like those used for refining of edible oils. The products are generally supplied in a particle size range between 0.3 and 0.6 mm, with specific surface between 200 and 400 m$^2$/g and ion exchange capacity (IEC) between 30 and 60 meq./100 g.

Synthetic silicates, like Al silicates, Mg silicates, Zr silicates, can also be used in addition to the preferred acid-activated bentonites.

The use of zeolites to eliminate olefins from aromatic fractions is described in U.S. Pat. No. 4,795,550. Zeolites are definitely very reactive; however, formation of polymer byproducts that lead to very rapid deactivation of the catalyst bed occurs in their narrow pore system.

The lifetime of acid-activated bentonites in fixed bed reactors varies very sharply, depending on the process conditions, and lies between a few weeks and 1 year. By that point so much catalytic activity has been lost by the deactivation process that replacement of the catalyst is necessary. Process operators of such aromatic units are therefore interested in a highly active catalyst characterized by a long lifetime.

The goal of the present invention is to develop catalysts for elimination of olefins from aromatics or aromatic mixtures based on smectites with constant high catalytic activity and thus longer lifetime.

The object of the invention is the use of naturally acid smectites to eliminate olefins from aromatic or aromatic mixtures. Naturally acid smectites are known, but have only been used thus far as bleaching earth. It has been surprisingly found that they are also suitable as catalysts for the aforementioned purpose.

BRIEF DESCRIPTION OF THE DRAWING

The FIGURE shows results of the performance of Comparison Examples 1 and 2 and Examples 1, 2 and 3.

A naturally acid smectite having the following properties is preferably used:

(a) a specific surface area of about 50 to 200 m$^2$/g;

(b) an ion exchange capacity (IEC) for exchangeable cations totalling about 40 to 80 meq./100 g, in which the portion of the IEC of Al$^{3+}$ ions is about 5 to 70 meq./100/g, the proportion of the IEC of the alkali ions is less than about 2.0 meq./100 g and the proportion of the IEC of the alkaline earth ions is less than about 50 meq./100 g;

(c) a total acidity of more than about 5 mg KOH/g;

(d) a proportion of free alkaline earth metal or alkali metal ions less than 5 meq./100 g.

The naturally acid smectite is preferably used in the form of particles larger than about 0.1 mm.

The catalytic activity of the naturally acid smectites used according to the invention can be further improved by incorporating Al$^{3+}$ ions.

The object of the invention is therefore also a catalyst based on naturally acid smectites for removal of olefins from aromatics or aromatic mixtures, characterized in that its content of exchangeable Al$^{3+}$ cations is at least 5 meq./100 g greater than that of the naturally acid smectite.

The catalyst is preferably characterized by (a) a specific surface of about 50 to 200 m$^2$/g;

(b) an ion exchange capacity (IEC) for exchangeable cations totalling about 40 to 80 meq./100 g, in which the proportion of the IEC of the Al$^{3+}$ ions is about 10 to 70 meq./100 g, the proportion of the IEC of the alkali metal ions is less than about 2.0 meq./100 g and the proportion of the IEC of the alkaline earth metal ions is less than about 50 meq./100 g.

(c) a total acidity of more than about 10 mg KOH/g;

(d) a proportion of free alkaline earth or alkali metal ions less than 5 meq.

The content of exchangeable Al$^{3+}$ ions is preferably about 10 to 30 meq./100 g.

"Exchangeable Al$^{3+}$ ions" are understood to mean Al$^{3+}$ ions that are bonded to intermediate layer positions and not within the layers of the smectite clay mineral. They are chemically bonded in the sense of ion exchange so that they cannot be washed out with water. The content of exchangeable Al$^{3+}$ ions is determined when the total ion exchange capacity (IEC) is determined. A sample of the catalyst (2 g) is boiled under reflux for 1 hour of 100 mL in a 2N NH$_4$Cl solution and allowed to stand 16 hours at room temperature. The sample is then filtered and washed chloride-free. The total IEC is initially determined by determining the NH$_4^+$ ions incorporated in the lattice. For this purpose the content of ammonium ions in the NH$_4$-exchanged catalyst is determined according to Kjeldahl. The content of exchangeable Al$^{3+}$ ions is determined spectrophotometrically in the filtrate of the NH$_4$Cl boiling solution and expressed in meq./100 g of catalyst. The content of alkali and alkaline earth metal ions in the filtrate of the NH$_4$Cl boiling solution is determined in the same manner.

The total IEC and the percentage of exchangeable cations of the reference substances are determined according to the same method.

The catalyst according to the invention can contain free $Al^{3+}$ ions on the surface, in the pores and in the intermediate grain volume in addition to the exchangeable $Al^{3+}$ ions. These $Al^{3+}$ ions can be eliminated by simple washing of the catalyst with water.

For this purpose a sample of the catalyst (10 g) is washed five times with 100 mL of water each time at 25° C. in a suction filter before boiling with the $NH_4Cl$ solution until aluminum is no longer detectable in the last washing water fraction. The aluminum in the combined washing waters is again determined spectrophotometrically. The other free cations can also be determined in the same manner.

Determination of the IEC and the proportion of individual ions in the overall IEC, as well as determination of the free cations, can also be carried out in the smectite reference materials. The result here simulates an unduly high content of exchangeable calcium or magnesium ions. This is caused by the fact that the smectite starting material is often contaminated with calcium and/or magnesium carbonate, which are dissolved during boiling with the $NH_4Cl$ solution.

It is assumed that both the exchangeable $Al^{3+}$ ions and the free $Al^{3+}$ ions have a catalytic effect in the manner of Lewis acids. Lewis acids (especially aluminum chloride) have only been used thus far in homogeneous catalysis. It is therefore surprising that the exchangeably bonded $Al^{3+}$ ions in the heterogeneous catalysts according to the invention also act as Lewis acids. It is particularly surprising that the catalytic effect of exchangeable $Al^{3+}$ cations is stronger than the catalytic effect of the free $Al^{3+}$ ions.

Another object of the invention is a process for production of the catalyst, characterized in that a naturally acid smectite starting material is treated with an aluminum salt solution whose amount is adjusted so that the content of exchangeable $Al^{3+}$ ion is increased by at least 10 meq./100 g and that a percentage of free $Al^{3+}$ ions is optionally still present.

In this case one generally starts from a naturally acid smectite starting material with a content of exchangeable $Al^{3+}$ ions of less than 5 meq./100 g, although one can also start from a material with a higher content of exchangeable $Al^{3+}$ ions. The catalytic activity of this type of starting material, which already meets the conditions for a catalyst according to the invention, can be further increased by incorporation of additional $Al^{3+}$ ions. Treatment according to the invention can therefore be conducted in two or more stages.

In the first preferred variant of the process according to the invention one proceeds by using the aluminum salt in a one- to five-fold molar excess based on the IEC, carrying out exchange of the $Al^{3+}$ ions relative to mono- and divalent cations and then washing the catalyst to eliminate the free, i.e., water-soluble aluminum salts, as well as salts of the mono- and divalent cations, if these interfere in the overall process.

A suspension of the naturally acid smectite clay mineral (bleaching earth suspension) is impregnated with an aluminum salt solution, especially with an aluminum sulfate solution, during which direct ion exchange occurs. After several hours of exchange at room temperature or elevated temperature the excess aluminum ions are washed out, whereupon the exchanged bleaching earth product is dried. This is followed by a granulation process.

According to the second variant a granulate of a naturally acid bentonite (bleaching earth granulate) classified beforehand can be sprayed with excess aqueous aluminum sulfate solution, during which part of the $Al^{3+}$ ions are bonded exchangeably and another part of the $Al^{3+}$ ions are present in free form, i.e., only adsorbed. After spraying, the material is dried at about 80 to 150° C., preferably at about 100° C.

A few percent of aluminum salt is sufficient for significantly increased catalytic activity in both variants. In principle, various aluminum salts are suitable. For commercial and technical reasons aluminum sulfate is preferred over aluminum chloride.

According to both variants the catalyst enriched in $Al^{3+}$ ions can be converted to a granulate with a particle size of 0.1 mm.

Another object of the invention is use of the catalyst according to the invention to eliminate olefins from aromatics or aromatic mixtures.

The additional features stated in the claims and specification are defined as follows:

1. Specific surface area: According to the BET method (one-point method with nitrogen according to DIN 66131, in which the sample is first degassed 10 hours at 150° C.).
2. Total acidity: A sample of the catalyst (5 g) is suspended in 250 ml of a 5 weight percent sodium chloride solution at 95° C. and then filtered. The obtained clear filtrate is titrated with 0.1N KOH solution against phenolphthalein. The total acidity is expressed in mg KOH/100 g of catalyst.

The invention is explained in nonlimiting fashion by the following examples.

COMPARATIVE EXAMPLE 1

Production of a granulate from untreated bentonite 100 kg of a dried Bavarian calcium bentonite (Tonsil® 13 from Sud-Chemie AG) with the properties listed in Table 1 was ground and mixed with 32 kg of water for 10 minutes in a Drais intensive mixer and then pressed to an extrudate 2 mm thick on a single screw extruder.

The moist extrudate was dried at 110° C. for 10 hours and then ground in a roll breaker with a gap distance of 1 mm. The fraction was then screened between 0.3 mm and 0.6 mm.

COMPARATIVE EXAMPLE 2

Production of an unmodified bleaching earth granulate 100 kg of a bleaching earth in the form of an HCl-activated bentonite (Tonsil® Optimum FF from Sud-Chemie AG) with the properties listed in Table 1 was mixed with 45 kg of water for 10 minutes in the Drais intensive mixer and then pressed to an extrudate 2 mm thick on a single-screw extruder.

The moist extrudate was further treated as in comparative example 1.

EXAMPLE 1

Production of a granulate based on a naturally acid crude clay 100 kg of a naturally acid ground and dried crude clay with the properties listed in Table 1 was mixed with 35 kg of water for 10 minutes in a Drais intensive mixer and then pressed to an extrudate 2 mm thick on a single-screw extruder.

The moist extrudate was further treated according to comparative example 1.

EXAMPLE 2

Exchange of exchangeable $Al^{3+}$ ions in naturally acid bentonite 100 kg of the naturally acid bentonite of example 1 was dispersed in 1000 L of distilled water under vigorous agitation. After an agitation time of 3 hours 7.5 kg aluminum sulfate was added in solid form and the suspension was then agitated at room temperature for another 12 hours.

The aluminum sulfate-containing suspension was then dewatered on a filter press and washed with 1000 l of demineralized water. The wet filter cake was dried for 12 hours at 120° C.

The dried filter cake was then ground on a breaker and the fraction between 0.3 and 0.6 mm was screened. The properties of the catalyst so obtained are shown in Table 1.

aromatic mixture was taken every 24 hours via the time-controlled sampling valves and the bromine index determined.

The bromine index is plotted versus operating time (days) to evaluate catalytic activity. The results are shown in the accompanying Figure 1.

It is apparent that the acid-activated bentonite according to comparative example 2 has a longer lifetime than the untreated bentonite according to comparative example 1. The longest lifetime, however, is exhibited by the catalyst according to example 2, which contains only exchangeable $Al^{3+}$ cations. A somewhat shorter lifetime is exhibited by the naturally acid catalyst according to example 1 and the catalyst enriched with exchangeable and free $Al^{3+}$ ions according to example 3. It follows that the effect according to the invention is most pronounced when the catalyst is only enriched with exchangeably bonded $Al^{3+}$ ions.

TABLE 1

| Catalyst | BET surface area ($m^2/g$) | Ion exchange capacity (IEC) mg-equiv/100 g | | | | | | | Free $Al^{3+}$ cations (meq./100 g) | Total Acidity (mgKOH/g) |
| --- | --- | --- | --- | --- | --- | --- | --- | --- | --- | --- |
| | | Total | $Al^{3+}$ | $Fe^{3+}$ | $Ca^{2+}$ | $Mg^{2+}$ | $K^+$ | $Na^+$ | | |
| Comparative example 1 | 70 | 63.7 | 0.2 | 6.5 | 38.0 | 44.0 | 3.5 | 1.5 | <0.1 | 0 |
| Comparative example 2 | 237 | 31.7 | 8.0 | 2.9 | 16.3 | 2.4 | 1.1 | 0.9 | <0.1 | 8.7 |
| Example 1 | 87 | 71.2 | 13.8 | 4.9 | 26.7 | 18.5 | 0.7 | 0.5 | 0.3 | 11.8 |
| Example 2 | 84 | 69.7 | 28.5 | 2.3 | 18.2 | 14.3 | 0.7 | 0.6 | 0.5 | 19.2 |
| Example 3 | 80 | 70.5 | 42.3 | 2.6 | 19.2 | 17.5 | 0.6 | 0.5 | 13.4 | 28.1 |

EXAMPLE 3

Exchange of exchangeable and free $Al^{3+}$ ions in naturally acid bentonite 100 kg of the granulate from example 1 was introduced to a pelletizer and then sprayed with 20 l of a 25% aluminum sulfate solution. The impregnated granulate was dried for 24 hours at 120° C.

The $Al^{3+}$ ions were partially incorporated in the lattice; they were partially situated on the surface of the material. The properties of the impregnated granulate are shown in Table 1.

APPLICATION EXAMPLE (Determination of catalytic activity of the catalysts during olefin elimination from aromatic mixtures)

An aromatic mixture obtained from sulfolane extraction (70 wt % benzene, 30 wt % toluene) with an olefin fraction corresponding to a bromine index of 50 mg $Br_2$/100 g (according to ASTM D-1491) was fed with an HPLC pump through an HPLC column in which the catalyst being investigated was present as packing (reactor volume 10 mL). The HPLC column is situated in a controllable thermostat in which the temperature was kept constant at 200° C. To avoid gas formation at these high temperatures a backpressure control was provided between the HPLC column and the electronically controlled sampling valves. A counterpressure of 50 bar was set on this backpressure controller.

An LHSV (liquid hourly space velocity) of 12 $h^{-1}$ was set by means of the HPLC pump. A sample of the purified

What is claimed is:

1. A catalyst for removing olefins from aromatic compounds or mixtures of aromatic compounds comprising
   a naturally acidic smectite containing exchangeable cations, wherein the naturally acidic smectite has a cation exchange capacity of about 40 to about 80 meq./100 g, wherein the exchangeable cations comprise $Al^{3+}$ cations which contribute about 5 to about 70 meq./100 g to the cation exchange capacity of the naturally acidic smectite and wherein the total acidity of the naturally acidic smectite is more than about 5 mg KOH/g.

2. The catalyst of claim 1 wherein the naturally acidic smectite has a specific surface area of approximately 50 to 200 $m^2/g$.

3. The catalyst of claim 1 wherein the exchangeable cations further comprise exchangeable alkali metal ions contributing less than about 2.0 meq./100 g to the cation exchange capacity of the naturally acidic smectite.

4. The catalyst of claim 1 wherein the exchangeable cations further comprise exchangeable alkaline earth metal ions contributing less than about 50 meq./100 g to the cation exchange capacity of the naturally acidic smectite.

5. The catalyst of claim 1 wherein the naturally acidic smectite has a total acidity of more than about 10 mg of KOH/g of the naturally acidic smectite.

6. The catalyst of claim 1 wherein the exchangeable cations further comprise free alkaline earth metal ions or alkaline metal ions in an amount of less than about 5 meq./100 g of the naturally acidic smectite.

7. The catalyst of claim 1 wherein the exchangeable $Al^{3+}$ ions contribute about 10 to about 30 meq./100 g to the cation exchange capacity of the naturally acidic smectite.

8. The catalyst of claim 1 wherein the naturally acidic smectite further comprises free $Al^{3+}$ ions.

9. The catalyst of claim 8 wherein the free $Al^{3+}$ ions are present on the surface, within the pores or in the intermediate particle volumes of the naturally acidic smectite.

10. The catalyst of claim 1 wherein the naturally acidic smectite is in the shape of particles with a diameter greater than about 0.1 mm.

11. A catalyst for removing olefins from aromatic compounds or mixtures comprising naturally acidic smectite particles containing exchangeable cations with a specific surface area of about 50 to 200 $m^2/g$, wherein the cation exchange capacity of the naturally acidic smectite particles is from about 40 to 80 meq./100 g, wherein the exchangeable cations comprise $Al^{3+}$ ions, which contribute about 10 to about 70 meq./100 g to the cation exchange capacity of the naturally acidic smectite, alkali metal cations, which contribute less than about 2.0 meq./100 g to the cation exchange capacity of the naturally acidic smectite and alkaline earth metal cations which contribute less than about 50 meq./100 g to the cation exchange capacity of the naturally acidic smectite and wherein the total acidity of the naturally acidic smectite is more than about 5 mg KOH/g.

12. The catalyst of claim 11 wherein the particles have a total acidity greater than about 10 mg KOH/g of the catalyst.

13. The catalyst of claim 11 wherein the naturally acidic smectite further comprises free alkaline earth metal or alkali metal ions in an amount less than about 5 meq./100 g of the naturally acidic smectite.

14. The catalyst of claim 11 wherein the $Al^{3+}$ ions contribute about 10 to about 30 meq./100 g of the catalyst to the cation exchange capacity of the naturally acidic smectite.

15. The catalyst of claim 11 wherein the naturally acidic smectite further comprises free $Al^{3+}$ cations on the surface of the particles, within pores of the particles or in intermediate particle volume.

16. The catalyst of claim 11 wherein the diameter of particles is greater than about 0.1 mm.

17. A process for the preparation of a catalyst for removing olefins from aromatic compounds or mixtures of aromatic compounds comprising treating a naturally acidic smectite starting material with an aluminum salt solution, wherein the salt solution comprises $Al^{3+}$ ions in a concentration of at least about 10 meq./100 g of the catalyst and wherein the total acidity of the naturally acidic smectite is more than about 5 mg KOH/g.

18. The process of claim 17 further comprising treating the naturally acidic smectite starting material with $Al^{3+}$ ions in a molar excess of about 1 to about 5 times the cation exchange capacity of the naturally acidic smectite to form a catalyst precursor material and washing said catalyst precursor.

19. The process of claim 18 further comprising molding the washed catalyst precursor into particles with a diameter greater than about 0.1 mm.

20. A process for removal of olefins from aromatic compounds or mixtures of aromatic compounds comprising feeding the aromatic compounds or mixtures of aromatic compounds across a bed of catalyst, wherein the catalyst comprises a naturally acidic smectite treated with a salt solution, wherein the salt solution comprises $Al^{3+}$ cations in a concentration of at least about 5 meq./100 g of the catalyst and wherein the total acidity of the naturally acidic smectite is more than about 5 mg KOH/g.

21. The process of claim 20 wherein the naturally acidic smectite further comprises alkali metal ions and alkaline earth metal ions, wherein the alkali metal ions contribute less than about 7.0 meq./100 g and the alkaline earth ions contribute less than about 50 meq./100 g to the cation exchange capacity of the naturally acidic smectite.

22. The process of claim 18 wherein the naturally acidic smectite further comprises free $Al^{3+}$ ions.

* * * * *